United States Patent
Chaumonnot et al.

(10) Patent No.: US 9,758,442 B2
(45) Date of Patent: Sep. 12, 2017

(54) METHOD FOR DEHYDRATING AND ISOMERISING ALCOHOLS USING A NON-ZEOLITE ALUMINOSILICATE SOLID

(71) Applicant: IFP ENERGIES NOUVELLES, Rueil-Malmaison (FR)

(72) Inventors: Alexandra Chaumonnot, Lyons (FR); Vincent Coupard, Villeurbanne (FR); Sylvie Maury, Saint Maurice d'Argoire (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 327 days.

(21) Appl. No.: 14/388,859

(22) PCT Filed: Mar. 25, 2013

(86) PCT No.: PCT/FR2013/050630
§ 371 (c)(1),
(2) Date: Sep. 29, 2014

(87) PCT Pub. No.: WO2013/144491
PCT Pub. Date: Oct. 3, 2013

(65) Prior Publication Data
US 2015/0057481 A1 Feb. 26, 2015

(30) Foreign Application Priority Data
Mar. 29, 2012 (FR) .................................. 12 00951

(51) Int. Cl.
*C07C 1/24* (2006.01)
*B01J 35/10* (2006.01)
*B01J 21/12* (2006.01)
*C07C 5/27* (2006.01)
*B01J 37/00* (2006.01)

(52) U.S. Cl.
CPC ............... *C07C 1/24* (2013.01); *B01J 21/12* (2013.01); *B01J 35/108* (2013.01); *B01J 35/1019* (2013.01); *B01J 35/1023* (2013.01); *B01J 35/1038* (2013.01); *B01J 35/1042* (2013.01); *B01J 35/1061* (2013.01); *B01J 37/0009* (2013.01); *C07C 5/2772* (2013.01); *C07C 2529/03* (2013.01)

(58) Field of Classification Search
CPC ...... B01J 21/12; B01J 37/0009; B01J 35/108; B01J 35/1019; B01J 35/1023; B01J 35/1038; B01J 35/1042; B01J 35/1061; C07C 5/2772; C07C 1/24; C07C 11/09; C07C 11/08

See application file for complete search history.

(56) References Cited

U.S. PATENT DOCUMENTS

| | | | |
|---|---|---|---|
| 5,545,793 A | 8/1996 | Travers et al. | |
| 7,572,946 B2 * | 8/2009 | Lacombe ................. | C07C 2/10 585/520 |
| 8,137,532 B2 * | 3/2012 | Euzen ...................... | B01J 21/12 208/111.3 |
| 2013/0137908 A1 * | 5/2013 | Coupard ................. | C07C 1/24 585/313 |
| 2013/0204057 A1 | 8/2013 | Adam et al. | |

FOREIGN PATENT DOCUMENTS

| | | | | |
|---|---|---|---|---|
| EP | 0659719 A1 | 6/1995 | | |
| FR | WO 2011154621 A1 * | 12/2011 | ............... | C07C 1/24 |
| WO | 2011113834 A1 | 9/2011 | | |

OTHER PUBLICATIONS

International Search Report from PCT/FR2013/050630 dated Jun. 11, 2013.
R.A. Comelli et al. "Transformation of C1-C4 Alcohols into Hydrocarbons on an Amorphous Silica-Alumina Catalyst" Applied Catalysis, [1988], vol. 36, pp. 299-306.

* cited by examiner

*Primary Examiner* — In Suk Bullock
*Assistant Examiner* — Jason Chong
(74) *Attorney, Agent, or Firm* — Millen White Zelano and Branigan, PC; John Sopp; Anthony Zelano

(57) ABSTRACT

Process for simultaneous dehydration and skeletal isomerization of a feedstock that comprises at least one $C_4$ monoalcohol and that contains between 0.5 and 50% water, for the purpose of producing $C_4$ alkenes, with said process operating at a temperature of between 250 and 550° C., under a pressure of between 0.1 and 1 MPa, with an hourly volumetric flow rate of between 0.1 and 10 $h^{-1}$, characterized in that it uses a catalyst that comprises at least one non-zeolitic aluminosilicate-type solid.

17 Claims, No Drawings

METHOD FOR DEHYDRATING AND ISOMERISING ALCOHOLS USING A NON-ZEOLITE ALUMINOSILICATE SOLID

TECHNICAL FIELD OF THE INVENTION

This invention relates to an improved process for the production of $C_4$ alkenes or butenes from an alcohol feedstock. The alcohol feedstock that is used can be obtained by chemical processes or by fermentation processes starting from carbohydrates. This process uses a catalyst that is based on a non-zeolitic aluminosilicate-type solid that has particular textural and acidity properties.

The alkenes that are obtained, and in particular isobutene and butene-1, have an important advantage in the field of petrochemical industry and organic synthesis, with the isobutene being a key compound in the chemistry of major intermediate compounds.

PRIOR ART

The dehydration of the $C_4$ monoalcohols has been studied for many years, primarily as a method for synthesis or for purification of isobutene. Catalysts based on mineral acid, $FeCl_2$ salt, and metal oxides such as alumina or zeolites have been used for this application. The article by Adkins et al., J. Am. Chem. Soc. 1925, 47, 1163 will be cited, where it is noted that alumina, after activation in air, is effective for a short period for dehydration of numerous alcohols. The authors note that only the activation in air makes it possible to make the alumina active in this application.

The article by Makarova et al., J. Catal., 1994, 149, 36 will also be cited, where it is taught that the MFI zeolite (ZSM-5) and the amorphous silica-aluminas are also active in dehydration of linear butanols. The positional isomerization of formed butenes is mentioned. However, no skeletal isomerization is demonstrated. In contrast, the formation of ethers (dibutyl ethers) is observed.

The works of P. Berteau et al., described in Applied Catalysis, 1991, 70, 307, which studied the acido-basic properties of silica-aluminas with variable contents of Si and Al, will also be cited. The variable acido-basic properties were correlated with the catalytic properties in the dehydration reaction of 1-butanol. The authors conclude that in the alumina-rich solids (low Bronsted acidity), only the dehydration of 1-butanol into butene-1 as well as the formation of ether (dibutyl ether) take place. In contrast, in the silica-rich solids (more pronounced Bronsted acidity), the dehydration into butene-1 and the rapid positional isomerization into butene-2 cis and trans take place. No reaction of skeletal isomerization is observed.

The U.S. Pat. No. 5,545,793 describes a process for isomerization of the skeleton and the position of the double bond of $C_4$ olefins, using an alumina-based solid having undergone a particular shaping in the presence of a polyorganosiloxane. This reaction is used in a process where the water is co-introduced with the olefinic feedstock so as to limit the parasitic reactions. The tests provided in the example indicate performances obtained at temperatures of higher than 400° C. after 1 hour of operation, which is relatively short and can only allow one to think that the stability of the catalyst over time remains perfectible. With the skeletal isomerization reaction always being accompanied by undesirable secondary reactions, a loss of activity of the catalyst can be explained by coking reactions.

The works described in Applied Catalysis A: General, 2001, 214, 251 relate to the simultaneous dehydration and skeletal and positional isomerization of the double bond in $C_4$ alcohols. In these works, gamma-aluminas that are optionally activated with sulfuric acid have been used at very low GHSV (Gas Hourly Space Velocity: mass flow rate of feedstock per volume of catalyst per hour) with different monoalcohols comprising an aliphatic chain with 4 carbons to evaluate their selectivity in terms of production of corresponding olefins and in other undesired products such as methane, ethane, ethylene, propane, propylene, and the $C_5^+$ products. It is thus demonstrated that an alumina that is activated with sulfuric acid is more active and more selective than an alumina of commercial origin for the combined application targeted, namely the dehydration combined with the isomerization of the skeleton and the position of the double bond of the resulting olefins. According to this document, it therefore seems that the most acidic alumina possible is necessary for jointly implementing the dehydration and the isomerization of $C_4$ monoalcohols. The selectivities of linear butenes starting from isobutanol (skeletal isomerization) are not, however, improved by the activation of alumina with sulfuric acid. No mention is made of the stability of the performances of this solid over time under load. It should be noted that, in a publication by the same team, Applied Catalysis A, 2000, 203, 5, the skeletal-isomerization activity of n-butenes, starting from an alumina activated with sulfuric acid that is prepared according to the same operating procedure, lasted only 5 to 6 hours, with these solids requiring regeneration in air every 6 hours.

Chadwick et al. describe in Applied Catalysis A, 2001, 403, 1 the one-stage dehydration and isomerization of n-butanol for forming isobutene on unmodified commercial acid zeolites. They compare in particular the performances of zeolites of a mean size of channels (10 MR) such as theta-1, ZSM-23, ZSM-5, ferrierite, SAPO-11 and Y, with the most stable zeolites being the monodimensional ones (theta-1 and ZSM-23), ferrierite being deactivated and SAPO-11 being dealuminified.

It should be noted that thus far, the large majority of publications focused on the production of isobutene starting from linear butanols, with the isobutene being a key molecule of petrochemistry and for the synthesis of gasoline additives such as ETBE and MTBE. In addition, the linear butanols were more easily produced by conventional fermentation methods (ABE) than isobutanol. Nevertheless, recent developments have made it possible to greatly improve the isobutanol yields, making this feedstock accessible and available at an attractive cost.

The patent application WO 2011/113834 A1 describes a process for simultaneous dehydration and skeletal isomerization of isobutanol for the purpose of producing corresponding olefins on crystalline silicate catalysts, which may or may not be dealuminified, may or may not be modified with phosphorus, of the group FER, MWW, EUO, MFS, ZSM-48, MTT, MFI, MEL or TON having an Si/Al ratio that is greater than 10, silicoaluminophosphate molecular sieves of the group AEL, or silica-alumina, zirconia-alumina, titanium-alumina, or fluorine-alumina. In the examples, the authors demonstrate a very good selectivity of isomers of the isobutene with a high WHSV (feedstock mass per catalyst mass per hour) on H-FER zeolite and on phosphorus-modified HZSM-5, with the modified ZSM-5 bringing about the formation of a maximum 10% of heavy compounds ($C_5^+$). No concept of stability of these performances is mentioned in this document. The only other catalyst shown is gamma-alumina.

The dehydration of $C_4$ alcohols on acid solids is generally accompanied by the positional isomerization of the alkene that is formed. These two reactions are actually concomitant, since the positional isomerization of the double bond of the alkene is as fast as the dehydration reaction of the $C_4$ monoalcohol. In the case of isobutanol, the isobutene that is initially formed becomes protonated easily (formation of a tertiary carbocation) and can then undergo secondary reactions, in particular of dimerization and then of cyclization, running the risk of bringing about the formation of undesired secondary products.

OBJECTS AND ADVANTAGES OF THE INVENTION

This invention has as its object a process for simultaneous dehydration and skeletal isomerization of a feedstock that comprises at least one $C_4$ monoalcohol and that contains between 0.5 and 50% by weight of water for the purpose of producing $C_4$ alkenes, in which a catalyst is used that comprises at least one non-zeolitic aluminosilicate-type solid that has particular textural and acidity properties obtained by the particular method for preparation of said solid. The process that uses said catalyst makes it possible to have a service life of the catalyst, an activity and a selectivity of linear butenes that are improved over time, as well as a limitation of the oligomerization reactions relative to the processes of the prior art.

DETAILED DESCRIPTION OF THE INVENTION

This invention has as its object a process for simultaneous dehydration and skeletal isomerization of a feedstock that comprises at least one $C_4$ monoalcohol and that contains between 0.5 and 50% water for the purpose of producing $C_4$ alkenes, with said process operating at a temperature of between 250 and 550° C., under a pressure of between 0.1 and 1 MPa, and with an hourly volumetric flow rate of between 0.1 and 10 $h^{-1}$, characterized in that it uses a catalyst that comprises at least one non-zeolitic aluminosilicate-type solid, with the silica content by mass of said solid being between 4 and 95% by weight of said solid, with said solid having the following characteristics:

A total pore volume, measured by mercury intrusion porosimetry, encompassed between 0.1 ml/g and 0.7 ml/g, A total pore volume, measured by nitrogen adsorption isotherm, encompassed between 0.1 ml/g and 0.7 ml/g, A BET specific surface area encompassed between 100 and 550 $m^2/g$, A pore volume, measured by mercury intrusion porosimetry, encompassed in the pores with a diameter of greater than 140 Å, of less than 0.1 ml/g, A pore volume, measured by mercury intrusion porosimetry, encompassed in the pores with a diameter of greater than 500 Å, of less than 0.1 ml/g, A mean pore diameter encompassed between 20 and 140 Å, with said solid being prepared according to a process comprising at least one stage a) for mixing at least one aluminum compound that is partially soluble in acid medium with either at least one silicic compound that is totally soluble in the reaction mixture or a combination formed by at least one silicic compound and at least one aluminum compound, with said silicic and aluminum compounds being totally soluble in the reaction mixture in such a way as to form a precursor solid of said catalyst, a stage b) for shaping said precursor solid, a stage c) for heat treatment and/or hydrothermal treatment, with said stage c) being carried out before or after said stage b).

Hourly volumetric flow rate (also designated by the term VVH) is defined as the ratio of the volumetric flow rate of feedstock in $m^3/h$ at 15° C., 1 atm per volume of catalyst.

In accordance with the invention, the feedstock comprises at least one $C_4$ monoalcohol, with said $C_4$ monoalcohol being selected from among 1-butanol, 2-butanol, isobutanol and tert-butanol, taken by itself or in a mixture. In a preferred way, the feedstock for the most part comprises isobutanol. For the most part means that the mass ratio of isobutanol to all of the $C_4$ monoalcohols is greater than 50%, preferably greater than 70%, and more preferably greater than 80%.

In accordance with the invention, the feedstock contains 0.5 to 50% by weight of water. It can also contain at most 10% by weight of impurities linked to methods for obtaining the feedstock (nitrogen, acids, aldehydes, non-$C_4$ alcohols, primarily).

The presence of water in the process, regardless of whether it is introduced with the feedstock or whether it results from the dehydration reaction of alcohol, advantageously makes it possible to limit the oligomerization reactions, inevitable during the skeletal isomerization reaction, and therefore to improve the selectivity of the catalyst.

The concentration of water in the reactor is adjusted between 0.5% by weight relative to the alcohol and up to 50% by weight. Beyond this dilution, the process becomes difficult to justify in terms of energy. It will be possible to use a device of the type for mechanical recompression of vapors between the feedstock and the reactor or else in products for minimizing the energy consumption of the process.

In accordance with the invention, said process for simultaneous dehydration and skeletal isomerization is performed at a temperature of between 250 and 550° C., preferably between 300 and 450° C., under a pressure of between 0.1 and 1 MPa, preferably between 0.1 and 0.5 MPa, with an hourly volumetric flow rate of between 0.1 and 10 $h^{-1}$, preferably between 0.7 and 5 $h^{-1}$, and more preferably between 2 and 4 $h^{-1}$.

The reaction unit that is provided with catalyst can be used in a fixed bed and in a moving bed, preferably in an adiabatic fixed bed. The reaction is carried out in the gaseous phase with upward or downward flow, in one/several reactors with reheating between each reaction stage that makes it possible to compensate for the overall endothermicity. To reduce the losses of feedstock in the reactor, radial reactor technologies are preferably used, where the catalyst is placed between vertical internals (grids or diffusers) and where the thickness of the catalyst layer through which the reactive fluid passes is minimized without thereby resorting to reactors with an atypical ratio between diameter and height (larger than 1). The catalyst is regenerated periodically. In the case of use in a fixed bed, said reaction unit alternatively carries out the reactions for the production of $C_4$ alkenes and the regeneration of said catalyst in such a way as to eliminate the coke that is deposited on the surface of said catalyst during said reactions. In the case of an alternative use in a moving bed, said catalyst can be transported between said reaction unit and a regeneration unit.

So as to jointly carry out the dehydration of C4 monoalcohols and the reaction of skeletal isomerization of the alkene obtained by said dehydration in the best manner possible, this invention claims the use of a catalyst that comprises at least one non-zeolitic aluminosilicate-type solid that has particular textural and acidity properties. The phrase particular textural and acidity properties is defined in terms of this invention as a catalyst based on a non-zeolitic aluminosilicate-type solid that is essentially mesoporous and that has an acidity, essentially of the Bronsted type, that is adequate for optimally carrying out the dehydration of the monoalcohol combined with the isomerization of the skeleton and the position of the double bond of the resulting olefins, without thereby being too strong, which would lead to the formation of $C_5^+$ products via undesirable secondary oligomerization reactions.

Description of the Non-Zeolitic Aluminosilicate-Type Solid Encompassed in the Catalyst that is Used According to the Invention Said aluminosilicate-type solid is a solid of aluminosilicic nature, i.e., an inorganic oxide solid based on the elements aluminum and silicon, non-zeolitic and essentially mesoporous. The characteristics of said solid are the following, with the percentages by weight being determined relative to the total weight of said solid:

The silica content by mass ($SiO_2$) is between 4% and 95% by weight, preferably between 4 and 25% by weight or between 35 and 95% by weight, in a more preferred manner between 4% and 15% by weight or between 35% and 50% by weight, and in an even more preferred manner between 4% and 15% by weight, The content of cationic impurities is generally less than 0.1% by weight, in a preferred manner less than 0.05% by weight, and in an even more preferred manner less than 0.025% by weight. Content of cationic impurities is defined as the total content of alkalines, in particular of $Na^+$ cations, The content of anionic impurities is generally less than 1% by weight, in a preferred manner less than 0.5% by weight, and in an even more preferred manner less than 0.1% by weight. The anionic impurities that are present in said aluminosilicate-type solid are particularly halides, in particular chlorides, as well as sulfates and nitrates, The mean pore diameter, denoted $D_{mean}$, of the solid measured by mercury intrusion porosimetry, is between 20 and 140 Å, preferably between 40 and 120 Å, and in an even more preferred manner between 50 and 100 Å, The ratio between the volume V2, measured by mercury intrusion porosimetry and occupied by the pores with a diameter of between $D_{mean}-30$ Å and $D_{mean}+30$ Å, to the total pore volume, also measured by mercury intrusion porosimetry, is greater than 0.6, preferably greater than 0.7, and in an even more preferred manner greater than 0.8, The volume V3 occupied by the pores with a diameter of greater than $D_{mean}+30$ Å, measured by mercury intrusion porosimetry, is less than 0.1 ml/g, in a preferred manner less than 0.06 ml/g, and in an even more preferred manner less than 0.04 ml/g, The ratio between the volume V5, measured by mercury intrusion porosimetry and occupied by the pores with a diameter of between $D_{mean}-15$ Å and $D_{mean}+15$ Å, to the volume V2 above, also measured by mercury intrusion porosimetry, is greater than 0.6, preferably greater than 0.7, and in an even more preferred manner greater than 0.8, The volume V6 occupied by the pores with a diameter of greater than $D_{mean}+15$ Å, measured by mercury intrusion porosimetry, is less than 0.2 ml/g, in a preferred manner less than 0.1 ml/g, and in an even more preferred manner less than 0.05 ml/g, The total pore volume, measured by mercury intrusion porosimetry, is between 0.1 ml/g and 0.7 ml/g, in a preferred manner between 0.1 ml/g and 0.6 ml/g, and in an even more preferred manner between 0.1 ml/g and 0.5 ml/g, The total pore volume, measured by nitrogen adsorption isotherm, is between 0.1 ml/g and 0.7 ml/g, in a preferred manner between 0.1 ml/g and 0.6 ml/g, and in an even more preferred manner between 0.1 ml/g and 0.5 ml/g, The BET specific surface area is between 100 and 550 $m^2/g$, preferably between 150 and 500 $m^2/g$, in a more preferred manner between 150 and 350 $m^2/g$, and in an even more preferred manner between 150 and 250 $m^2/g$, The adsorption surface area, which is defined based on the branch of the hysteresis with adsorption of the nitrogen of the isotherm for pores with a diameter of between 3 and 200 nm, is such that the ratio between the adsorption surface area and the BET surface area is greater than 0.5, in a preferred manner greater than 0.65, and in a more preferred manner greater than 0.8, The pore volume, measured by mercury intrusion porosimetry, encompassed in the pores with a diameter of greater than 140 Å, is less than 0.1 ml/g, preferably less than 0.05 ml/g, and an even more preferred manner less than 0.03 ml/g, The pore volume, measured by mercury intrusion porosimetry, encompassed in the pores with a diameter of greater than 160 Å, is less than 0.1 ml/g, preferably less than 0.05 ml/g, and in an even more preferred manner less than 0.025 ml/g, The pore volume, measured by mercury intrusion porosimetry, encompassed in the pores with a diameter of greater than 200 Å, is less than 0.1 ml/g, preferably less than 0.075 ml/g, and in an even more preferred manner less than 0.05 ml/g, The pore volume, measured by mercury intrusion porosimetry, encompassed in the pores with a diameter of greater than 500 Å, is less than 0.1 ml/g, preferably less than 0.05 ml/g, in a more preferred manner less than 0.02 ml/g, and in an even more preferred manner less than 0.01 ml/g.

The non-zeolitic aluminosilicate-type solid is essentially mesoporous, i.e., the mesopore volume represents at least 85% of the total pore volume, in a preferred way at least 90% of the total pore volume, and in an even more preferred way at least 97% of the total pore volume.

The textural data provided above, characterizing said non-zeolitic aluminosilicate-type solid, are determined by nitrogen adsorption isotherm and by mercury intrusion porosimetry. The nitrogen adsorption isotherm analysis corresponding to the physical adsorption of nitrogen molecules in the porosity of said solid via a gradual increase of the pressure at constant temperature gives information on the particular textural characteristics (diameter of pores, type of porosity, specific surface area) of the non-zeolitic aluminosilicate-type solid encompassed in the catalyst that is used according to the invention. In particular, it makes it possible to access the specific surface area and the mesopore distribution of said solid. Specific surface area is defined as the BET specific surface area ($S_{BET}$ in $m^2/g$) determined by nitrogen adsorption in accordance with the ASTM D 3663-78 standard established starting from the BRUNAUER-EMMETT-TELLER method described in the periodical "The Journal of American Society," 1938, 60, 309. The pore distribution that is representative of a population of mesopores centered in a range of 1.5 to 50 nm is determined by the Barrett-Joyner-Halenda (BJH) model. The nitrogen adsorption-desorption isotherm according to the BJH model is described in the periodical "The Journal of American Society," 1951, 73, 373, written by E. P. Barrett, L. G. Joyner, and P. P. Halenda. In the disclosure above, the "total pore volume" corresponds to the volume measured for $P/P_o=0.99$, pressure for which it is assumed that nitrogen has filled all of the pores. In conclusion, the name "adsorption surface" relates to the surface measured on the branch of the adsorption isotherm. Reference will be made to, for example, the article by A. Lecloux in "Mémoires de la Société Royale des Sciences de Liège," 1971, $6^{th}$ Series, Volume I, Section 4, 169. In the disclosure above, the "pore volume" corresponds to the volume measured by mercury intrusion porosimetry according to the standard ASTM D4284-83 at a maximum pressure of 4,000 bar, using a surface tension of 484 dyne/cm and a contact angle for the non-zeolitic aluminosilicate-type solid encompassed in the catalyst that is used according to the invention of 140°. The mercury mean diameter is defined as being a diameter such that all of the pores of a size smaller than this diameter constitute 50% of the pore volume ($V_{Hg}$) in an interval of between 36 Å and 1,000 Å. The wetting angle was assumed to be equal to 140° by following the recommendations of the work "Techniques de l'ingénieur, traité analyse et caractérisation," 1050, by J. Charpin and B. Rasneur. So as to obtain better precision, the value of the mercury volume in ml/g provided in the following text corresponds to the value of the total mercury volume in ml/g measured on the sample minus the value of the mercury volume in ml/g measured on the same sample for a pressure corresponding to 30 psi (approximately 2 bar). So as to better characterize the resulting pore distribution of the analysis by mercury intrusion, the following pore distribution criteria are defined: the volume V2 corresponds to the volume contained in the pores with a diameter that is greater than or equal to the mean diameter minus 30 Å and less than or equal to the mean diameter plus 30 Å, the volume V3 corresponds to the volume contained in the pores with a diameter that is greater than or equal to the mean diameter plus 30 Å, the volume V5 corresponds to the volume contained in the pores with a diameter that is greater than or equal to the mean diameter minus 15 Å and less than or equal to the mean diameter plus 15 Å, and the volume V6 corresponds to the volume contained in the pores with a diameter that is greater than or equal to the mean diameter plus 15 Å.

The packing density of said solid is greater than 0.40 g/cm³, in a preferred manner greater than 0.45 g/cm³, and in a very preferred manner greater than 0.50 g/cm³.

Said non-zeolitic aluminosilicate-type solid is preferably a homogeneous aluminosilicate on the micrometer scale, and even on the nanometer scale. Homogeneous is defined as an aluminosilicate solid that consists of a single alumina-silica zone, with said zone at any point having a local Si/Al ratio (measured, for example, by EDX (Energy Dispersive Spectroscopy X-Ray) analysis combined with the TEM), equal to the overall Si/Al ratio determined by X-fluorescence.

Said non-zeolitic aluminosilicate-type solid has an acidity, essentially of the Bronsted type, that is adequate for optimally carrying out the dehydration of the monoalcohol combined with the isomerization of the skeleton and the position of the double bond of the resulting olefins, without thereby being too strong, which would lead to the formation of $C_5+$ products via undesirable secondary oligomerization reactions.

The acidity of said non-zeolitic aluminosilicate-type solid is advantageously determined by implementing a catalytic test for isomerization of the m-xylene into o- and p-xylene. This isomerization reaction actually requires the presence of Bronsted-type acid sites and is conventionally used for evaluating the Bronsted-type acidity of certain oxide solids, including aluminosilicate-type solids (Morin et al., J. Catal., 1996, 159, 296). This reaction is conducted at 350° C. under an inert atmosphere (nitrogen stream). The m-xylene is introduced at a PPH on the order of $0.25$ $h^{-1}$ (mass flow rate of feedstock per g of catalyst) in the reaction medium and passes through a fixed bed that consists of a mixture of extrudates or powder of the catalyst and silicon carbide. The analysis of the reaction products is done by gas chromatography; the value of the areas of each of the components makes possible the calculation of the conversion for a given time interval with A=area of the peak in µV·min:

$$\text{conversion} = \frac{\sum A_{products}}{A_{reagents} + \sum A_{products}}$$

The determination of the conversion makes possible the calculation of the isomass activity in $mmol \cdot h^{-1} \cdot g_{solid}^{-1}$ of said aluminosilicate-type solid for a given time interval with M=molar mass in $g \cdot mol^{-1}$ and m=mass in g:

$$\text{Activity} = \frac{\text{Conversion} \times \text{flow } rate_{xylene} \times density_{xylene}}{M_{xylene} \times m_{catalyst}}$$

To allow a better comparison of the samples to one another, the value of the selected activity is the one obtained at the end of ten minutes, i.e., the period during which the aluminosilicate-type solid is the most active. Within the framework of the invention, the acidity properties of said non-zeolitic aluminosilicate-type solid that lead to the optimal implementation of the dehydration of the monoalcohol combined with the isomerization of the skeleton and the position of the double bond of the resulting olefins are such that the value of the catalytic activity in an isomerization test of the m-xylene is between $0.02$ $mmol \cdot h^{-1} g_{solid}^{-1}$ and $0.4$ $mmol \cdot h^{-1} g_{solid}^{-1}$, preferably between $0.02$ $mmol \cdot h^{-1} g_{solid}^{-1}$ and $0.33$ $mmol \cdot h^{-1} g_{solid}^{-1}$, in an even more preferred way between $0.05$ $mmol \cdot h^{-1} g_{solid}^{-1}$ and $0.20$ $mmol \cdot h^{-1} g_{solid}^{-1}$, and in an even more preferred way between $0.05$ $mmol \cdot h^{-1} g_{solid}^{-1}$ and $0.15$ $mmol \cdot h^{-1} g_{solid}^{-1}$.

The overall composition of said non-zeolitic aluminosilicate-type solid, and in particular the sodium element content, can be determined by X fluorescence (FX) in said solvent in the powdered state or by atomic absorption (AA) after acid attack of said solid.

Process for Preparation of the Non-Zeolitic Aluminosilicate-Type Solid Encompassed in the Catalyst Used According to the Invention.

In accordance with the invention, said preparation process comprises at least one stage a) for mixing at least one partially soluble aluminum compound in an acid medium with either at least one silicic compound that is totally soluble in the reaction mixture or a combination formed by at least one silicic compound and at least one aluminum compound, with said silicic and aluminum compounds being totally soluble in the reaction mixture in such a way as to form a solid precursor with said aluminosilicate-type solid encompassed in the catalyst that is used according to the invention, a stage b) for shaping said precursor solid, and a stage c) for heat treatment and/or hydrothermal treatment, with said stage c) being carried out before or after said stage b).

The total dissolution property in the reaction mixture of said silicic compound or said silicic and aluminum compounds forming said combination was evaluated approximately according to the following method. A fixed quantity (15 g) of the silicic compound or said combination, preferably hydrated, is introduced into an aqueous medium with a preestablished pH. In a preferred manner, the concentration of solid, namely of silicic compound or silicic and aluminum compounds, added per liter of suspension, is 0.2 mol per liter. The pH of the solution is at least 12, and it can be obtained by use of an alkaline source. In a preferred manner, it is advantageous to use NaOH. The mixture is then stirred mechanically by a deflocculant-type turbine stirring mechanism for 30 minutes at 800 rpm. Once the stirring is finished, the mixture is centrifuged for 10 minutes at 3,000 rpm. The cake is separated from the supernatant liquid: the solution is filtered on a filter of porosity 4 with a 19 cm diameter. The drying and the calcination at 1000° C. of the 2 fractions, namely that of the cake and that of the supernatant liquid, are then carried out. The ratio R obtained by dividing the equivalent solid mass in the cake by the solid mass present in the supernatant liquid is then defined. The phrase totally soluble is defined as a ratio R that is greater than or equal to 0.9.

By the phrase "partially soluble in acid medium," it is understood that the contact of said aluminum compound with an acid solution, for example nitric acid or sulfuric acid, causes its partial dissolution before any addition or of at least one silicic compound that is totally soluble in the reaction mixture or a combination formed by at least one silicic compound and at least one aluminum compound, with said silicic and aluminum compounds being totally soluble in the reaction medium.

Said partial dissolution property of said aluminum compound was evaluated in an approximate manner according to the following method. A precise quantity of the aluminum compound in powder or in suspension is introduced into an aqueous medium of preset pH. The mixture is then stirred mechanically. Once the stirring is terminated, the mixture is left unstirred for 24 hours. In a preferred manner, the concentration of the solid that is introduced, expressed in terms of mol of $Al_2O_3$ per liter of suspension, is 0.5 mol per liter. The pH of the solution of the suspension is 2 and is obtained either by use of $HNO_3$ or by use of HCl, or by use of $HClO_4$. In a preferred manner, it is advantageous to use $HNO_3$. The distribution of aluminum is such that a first portion of the aluminum is present in a sedimented fraction and a second portion of the aluminum is present in a dissolved fraction. The distribution of aluminum in each of these two fractions was followed by metering of the aluminum by UV absorption. The dissolved fraction, also called supernatant, was ultrafiltered (polyether-sulfone membrane, millipore NMWL 30000) and digested in concentrated acid. The quantity of aluminum in said dissolved fraction (supernatant) corresponds to the non-sedimented aluminum compound and to dissolved aluminum, and the ultrafiltered fraction corresponds to the dissolved aluminum alone. The quantity of sedimented particles is derived from the theoretical concentration of aluminum in the suspension (by considering that the entire solid that is introduced is in suspension) and quantities of non-sedimented aluminum in suspension and aluminum dissolved in solution. The presence of sedimented particles characterizes the partial dissolution property. As soon as sedimented particles are observed with the naked eye, the aluminum compound is called "partially soluble." The aluminum precursors that are used for their partial dissolution property in the preparation of the non-zeolitic aluminosilicate-type solid encompassed in the catalyst used in the process of this invention are therefore differentiated from those used in the case of true co-precipitations, which are entirely soluble in acid medium, such as the cationic alumina salts including aluminum nitrate, for example, or in basic medium. The methods using said aluminum precursors used for their partial dissolution property are differentiated from true co-precipitations because one of the elements, in this case the aluminum compound, is partially soluble. True co-precipitation is defined as a process by which at least one aluminum compound and at least one silicic compound, totally soluble in a basic or acid medium, are brought into contact, simultaneously or sequentially, in the presence of at least one precipitating and/or co-precipitating compound as described in the U.S. Pat. No. 2,908,635, U.S. Pat. No. 3,423,332, U.S. Pat. No. 3,433,747, U.S. Pat. No. 3,451,947, U.S. Pat. No. 3,629,152 and U.S. Pat. No. 3,650,988.

This partial dissolution property is a property desired for the preparation of the non-zeolitic aluminosilicate-type solid encompassed in the catalyst that is used in the process of the invention.

The applicant discovered that the catalyst comprising a non-zeolitic aluminosilicate-type solid obtained according to a preparation process comprising at least said stage a), a stage b) for shaping said precursor solid, and a stage c) for heat treatment and/or hydrothermal treatment, said stage c) being carried out before or after said stage b), makes it possible to obtain a particularly high-performing catalyst for using the process for production of $C_4$ alkenes according to the invention. Actually, putting at least one aluminum compound that is partially soluble in acid medium in the presence of either at least one silicic compound that is totally soluble in the reaction mixture or a combination formed by at least one silicic compound and at least one aluminum compound, which are entirely soluble in the reaction mixture, corresponds to putting aluminum and silicic radicals of a specific size and chemical reactivity into said presence, thereby leading to controlled interactions between these radicals causing, in part, homogeneity on the micrometer scale, and even on the nanometer scale, of the aluminosilicate-type solid encompassed in the catalyst that is used for implementing the process for production of $C_4$ alkenes according to the invention.

Based on the chemical nature of the aluminum and silicic compounds used for the preparation of said solid, the control of the degree of interactivity between the silicic and aluminum radicals can be implemented in all of the stages of the preparation process preceding stage c) for heat treatment and/or hydrothermal treatment. For example and in a non-exhaustive way, the mixing of a partially soluble aluminum compound of the aluminum hydrate type, $Al_2O_3$, $nH_2O$ (boehmite) with a totally soluble silicic compound of the decationized orthosilicic acid type can be done in an aqueous medium under the influence of various controlled synthesis operating parameters (pH, temperature, etc.), or else the mixing of a partially soluble aluminum compound of the aluminum hydrate type, $Al_2O_3$, $nH_2O$ (boehmite) with a totally soluble silicic compound of the commercial silica colloidal-solution type (Ludox®) can be done during the shaping stage consecutively to the mechanical work generated during this shaping process.

Sources of Silica

The silicic compound used in said stage a) according to the invention is selected from the group formed by silicic acid, the sols of silicic acid, the water-soluble alkaline silicates, the cationic salts of silicon, for example hydrated sodium metasilicate, Ludox® in ammoniacal form or in alkaline form, quaternary ammonium silicates, taken by itself or in a mixture. The silica sol can be prepared according to one of the methods known to one skilled in the art. In a preferred manner, a decationized orthosilicic acid solution is prepared from a water-soluble alkaline silicate by ion exchange on a resin. In another embodiment, the Nyacol® or Nyacol® Nanotechnologies silica sols can be used. In another embodiment, the Aerosil® or Nyasil® silica powders can be used.

Totally Soluble Aluminosilicate Sources

The totally soluble hydrated aluminosilicates used according to the invention can be prepared by true co-precipitation under controlled stationary operating conditions (pH, concentration, temperature, mean dwell time) by reaction of a basic solution containing silicon, for example in the form of sodium silicate, optionally aluminum, for example in the form of sodium aluminate, with an acid solution containing at least one aluminum salt, for example aluminum sulfate. At least one carbonate or else $CO_2$ can optionally be added to the reaction medium.

Sources of Alumina

The aluminum compounds used according to the invention are partially soluble in acid medium. They are selected completely or in part in the group of aluminum compounds of general formula $Al_2O_3$, $nH_2O$. It is possible in particular to use hydrated alumina compounds such as: hydrargillite, gibbsite, bayerite, boehmite, pseudo-boehmite, and amorphous or essentially amorphous alumina gels, preferably boehmite, pseudo-boehmite, and amorphous or essentially amorphous alumina gels, taken by themselves or in a mixture. It is also possible to use the dehydrated forms of these compounds that consist of transition aluminas and that comprise at least one of the phases taken from the group: rho, chi, eta, gamma, kappa, theta and delta, which are differentiated essentially by the organization of their crystalline structure. The alpha-alumina commonly called corundum can be incorporated in a small proportion in the substrate.

This partial dissolution property is a desired property for the preparation of the non-zeolitic aluminosilicate-type solid encompassed in the catalyst used in the process of the invention. It applies to the hydrated alumina powders, to the atomized hydrated alumina powders, to the dispersions or suspensions of hydrated alumina or to any of their combinations, before any addition of a compound containing all or part of the silicon.

In accordance with the invention, the precursor solid described above is shaped during a stage b) by any technique known to one skilled in the art.

The shaping can be done, for example, by extrusion, by tabletting, by pelletizing, by pelletizing and crushing, by drying, by atomization, by the drop (oil-drop) coagulation method, by turntable granulation, or by any other method that is well known to one skilled in the art. More specifically, when the non-zeolitic aluminosilicate-type solid comes in the form of extrudates, it is possible to add or to remove water for adjusting the viscosity of the paste to be extruded. This stage can be carried out at any stage of the mixing step. To adjust the solid material content of the paste to be extruded so as to make it extrudable, it is also possible to add a compound that is solid for the most part and preferably an oxide or a hydrate. In a preferred manner, a hydrate will be used, and in an even more preferred manner, an aluminum hydrate will be used. The fire loss of this hydrate is greater than 15%. The content of acid added to the mixing before the shaping is less than 30%, preferably between 0.5 and 20% by weight of the anhydrous mass of silica and alumina engaged in the synthesis. The extrusion can be carried out by any conventional, commercially available tool. The paste obtained from the mixing is extruded through a die, for example using a piston or a single-screw or double-screw for extrusion. This extrusion stage can be carried out by any method that is known to one skilled in the art. Furthermore, said aluminosilicate-type solid may have been treated as is well known to one skilled in the art by additives for facilitating the shaping and/or improving the final mechanical properties of said catalyst. By way of example of additives, it is possible to cite in particular cellulose, carboxymethyl cellulose, carboxyethyl cellulose, xanthan gums, surfactants, flocculating agents such as polyacrylamides, carbon black, starches, stearic acid, polyacrylic alcohol, polyvinyl alcohol, biopolymers, glucose, polyethylene glycols, etc. The control of the porosity that is characteristic of the non-zeolitic aluminosilicate-type solid encompassed in the catalyst used in the process of the invention is partially performed during this stage for shaping the catalyst particles.

The non-zeolitic aluminosilicate-type solid encompassed in the catalyst used in the process of the invention comes in the form of spheres, spheroids, pellets or extrudates, preferably extrudates. In a very advantageous manner, said solid comes in the form of extrudates with a diameter of between 0.5 and 5 mm and more particularly between 0.7 and 2.5 mm. The shapes of said extrudates are cylindrical (which may or may not be hollow), braided cylindrical, multilobed (2, 3, 4, or 5 lobes, for example), or rings. The cylindrical and multilobed shapes are used in a preferred manner, but any other shape can be used.

Said non-zeolitic aluminosilicate-type solid generally has a crushing resistance of at least 70 N/cm and in a preferred manner greater than or equal to 100 N/cm. The crushing resistance is determined using the grain-to-grain crushing (EGG) test as described in the standards ASTM D4179-01, ASTM D6175-03.

In accordance with the invention, the preparation of said non-zeolitic aluminosilicate-type solid comprises a stage c) for heat treatment and/or hydrothermal treatment. Said stage c) makes it possible to ensure the degree of homogeneity on the micrometer scale, and even the nanometer scale, between the aluminum and silicic radicals necessary to the development of the acidity properties and textural properties of the non-zeolitic aluminosilicate-type solid encompassed in the catalyst used in the process for production of $C_4$ alkenes according to the invention.

In accordance with the invention, said stage c) is carried out before or after said stage b). The sequence in which said stages b) and c) are carried out does not have an effect on the characteristic of said non-zeolitic aluminosilicate-type solid.

In the case where stage c) is a heat treatment, said stage c) is advantageously a drying or a calcination.

The drying is done by any technique known to one skilled in the art.

The calcination is preferably done in the presence of molecular oxygen, for example by carrying out a flushing with air, at a temperature that is less than or equal to 1100° C. This treatment can be carried out, for example, in a flushed bed, in a swept bed, or under a static atmosphere. For example, the furnace that is used can be a rotary kiln or a vertical furnace with radial flushed layers. The conditions of calcination, temperature, and duration depend primarily on the maximum temperature of use of said solid, with the preferred calcination conditions ranging between more than one hour at 200° C. and less than one hour at 1100° C., preferably between 300 and 600° C. for a period of 1 to 24 hours, and in a more preferred way for a period of 2 to 12 hours. The calcination can be performed in the presence of water vapor. The final calcination optionally can be carried out in the presence of an acid or basic vapor. For example, the calcination can be carried out under partial pressure of ammonia. The hydrothermal treatments are carried out by any technique that is known by one skilled in the art. Hydrothermal treatment is defined as bringing into contact—at any stage of development—the solid with water in the vapor phase or liquid phase.

Hydrothermal treatment can be defined in particular as curing, steaming (steam treatment), autoclaving, calcination in moist air, and rehydration. Without this reducing the scope of the invention, such a treatment has the effect of making the silica component mobile. In a preferred way, the hydrothermal treatment is done by steaming in a furnace in the presence of water vapor. The temperature during the steaming can be between 300 and 1100° C., and preferably higher than 700° C. for a period of time of between 30 minutes and 12 hours, and preferably between 30 minutes and 4 hours. The water vapor content is greater than 20 g of water per kg of dry air, and preferably greater than 40 g of water per kg of dry air, and in a preferred manner greater than 100 g of water per kg of dry air. Such a treatment can, if necessary, replace the calcination treatment totally or partially.

Said solid can also advantageously be subjected to a hydrothermal treatment in a contained atmosphere. Hydrothermal treatment in a contained atmosphere is defined as a treatment of running through the autoclave in the presence of water under a temperature that is higher than ambient temperature. The temperature during autoclaving can be between 100 and 250° C. for a period of time of between 30 minutes and 6 hours, preferably between 30 minutes and 2 hours.

The non-zeolitic aluminosilicate-type solid encompassed in the catalyst used in the process of the invention can optionally undergo a particular post-treatment whose purpose is to adjust the acidity level of said solid. This post-treatment is a hydrothermal treatment and/or by chemical means usually used for carrying out the dealuminification of solids of a zeolitic nature. This optional stage can be carried out by any method known to one skilled in the art (refer to, for example, "Hydrocracking Science and Technology" of J. Scherzer and A. J. Gruia, Marcel Dekker, Inc., 1996).

It is also possible to add other components to the non-zeolitic aluminosilicate-type solid in such a way as to form the catalyst that is used according to the invention, with these components able to be introduced during said shaping stage b). Said components can be, in a non-exhaustive way, at least one porous oxide material that is selected from the group that is formed by alumina, silica, magnesia, clays, titanium oxide, zirconium oxide, lanthanum oxide, cerium oxide, aluminum phosphates, boron phosphates, and a mixture of at least two of the oxides cited above. Said porous oxide material can also be selected from among the mixtures of alumina-boron oxide, alumina-titanium oxide, alumina-zirconia, and titanium oxide-zirconia. The aluminates, for example the aluminates of magnesium, calcium, barium, manganese, iron, cobalt, nickel, copper and zinc, as well as the mixed aluminates, for example those containing at least two of the metals cited above, are advantageously used as porous oxide material. It is also possible to use titanates, for example titanates of zinc, nickel, and cobalt. It is also advantageously possible to use mixtures of alumina and silica and mixtures of alumina with other compounds such as the elements of group VIB, phosphorus, fluorine or boron. It is also possible to use clays that are simple, synthetic or natural, of the type dioctahedral phyllosilicate 2:1 or trioctahedral phyllosilicate 3:1, such as kaolinite, antigorite, chrysotile, montmorillonnite, beidellite, vermiculite, talc, hectorite, saponite, and laponite. These clays optionally can be delaminated. It is also advantageously possible to use mixtures of alumina and clay and mixtures of aluminosilicate and clay. Likewise, the use of at least one compound that is selected from the group that is formed by the family of molecular sieves of the crystallized aluminosilicate type and synthetic and natural zeolites such as the A zeolite, the Y zeolite, the fluorinated Y zeolite, the Y zeolite containing rare earths, USY, VUSY, SDUSY, the X zeolite, the L zeolite, the beta zeolite, the small-pore mordenite, the large-pore mordenite, and the following zeolites: omega, NU-10, ZSM-22, NU-85, NU-86, NU-87, NU-88, theta-1, ferrierite, ZSM-5, ZSM-48, ZSM-23, ZBM-30, EU-2, EU-11, silicalite, IM-5, IM-12, and EU-1 can be considered. Among the zeolites, it is usually preferred to use zeolites whose ratio of silicon/aluminum (Si/Al) framework atoms is greater than approximately 3/1. Advantageously, zeolites of faujasite structure and in particular stabilized and ultrastabilized Y zeolites (USY) are used either in the form at least partially exchanged with metal cations, for example cations of the alkaline-earth metals and/or cations of rare earth metals of atomic numbers 57 to 71 inclusive, or in hydrogen form (Atlas of Zeolite Framework Types, 6$^{th}$ Revised Edition, 2007, Ch. Baerlocher, L. B. McCusker, D. H. Olson). Finally, as a porous oxide material, it is possible to use at least one compound that is selected from the group that is formed by the family of non-crystallized aluminosilicate-type molecular sieves, such as the mesoporous silicas, the silicalite, the silicoaluminophosphates, the aluminophosphates, the ferrosilicates, the titanium silicoaluminates, the borosilicates, the chromosilicates, and the aluminophosphates of transition metals (including cobalt). The various mixtures that use at least two of the compounds cited above are also suitable.

Preferably, the catalyst according to the invention consists integrally of the non-zeolitic aluminosilicate-type solid.

EXAMPLES

Example 1

Synthesis of the Catalyst Based on Non-Zeolitic Aluminosilicate-Type Solid Used for the Process for Production of C4 Alkenes, According to the Description Given in this Invention (AS1)

The aluminum hydroxide powder was prepared according to the process described in the patent WO 00/01617. The mean size of the particles of aluminum hydroxide measured by laser granulometry is 40 microns. This powder is mixed with a silica sol obtained from the silicic acid prepared by decationizing resin exchange, and then filtered on resin of porosity 2. The concentrations of silica sol and aluminum hydroxide powder are adjusted in such a way as to obtain a final composition of 90% $Al_2O_3$ and 10% $SiO_2$. The solid, after filtration, is left in a dried state for one night at ambient temperature. The shaping is done by a mixing in a Z-arm mixing machine. The extrusion is done by passing the paste through a trilobed die of 2.5 mm. The thus obtained extrudates are dried at 150° C., calcined at 450° C. for 2 hours, and then steam-treated at 850° C. for 2 hours.

The characteristics of the substrate are as follows:

The composition of the silica-alumina substrate is 90% $Al_2O_3$ and 10% $SiO_2$.

The BET surface area is 220 m²/g.

The total pore volume, measured by nitrogen adsorption, is 0.53 ml/g.

The total pore volume, measured by mercury porosimetry, is 0.44 ml/g.

The mean pore diameter, measured by mercury porosimetry, is 79 Å.

The ratio between the volume V2, measured by mercury porosimetry, encompassed between $D_{mean}-30$ Å and $D_{mean}+30$ Å to the total pore volume measured by mercury porosimetry is 0.93.

The volume V3, measured by mercury porosimetry, encompassed in the pores with a diameter of greater than $D_{mean}+30$ Å is 0.017 ml/g.

The ratio between the volume V5, measured by mercury porosimetry, encompassed between $D_{mean}-15$ Å and $D_{mean}+15$ Å to the volume V2 above is 0.91.

The volume V6, measured by mercury porosimetry, encompassed in the pores with a diameter of greater than $D_{mean}+15$ Å is 0.02 ml/g.

The ratio between the adsorption surface area and the BET surface area is 1.

The pore volume, measured by mercury porosimetry, encompassed in the pores with a diameter of greater than 140 Å is 0.0017 ml/g.

The pore volume, measured by mercury porosimetry, encompassed in the pores with a diameter of greater than 160 Å is 0.0015 ml/g.

The pore volume, measured by mercury porosimetry, encompassed in the pores with a diameter of greater than 200 Å is 0.0013 ml/g.

The pore volume, measured by mercury porosimetry, is [sic] encompassed in the pores with a diameter of greater than 500 Å is 0.0007 ml/g.

The atomic sodium content is less than 40 ppm (detection limit of the analysis). The atomic sulfur content is less than 40 ppm.

The value of the catalytic activity in the isomerization test of m-xylene is 0.07 mmol·h⁻¹·$g_{solid}^{-1}$.

Example 2

Synthesis of a Catalyst Based on a Non-Zeolitic Aluminosilicate Solid not in Accordance with the Description Given in this Invention (AS2)

An aluminosilicate substrate not in accordance with the invention is prepared according to one of the synthesis protocols proposed in the U.S. Pat. No. 4,837,193 based on the true co-precipitation in aqueous medium of an aluminum precursor and a silicic precursor that are totally soluble in said medium by adding a basic compound. Thus, the solid is obtained by co-precipitation of a sodium metasilicate solution with an aluminum sulfate solution in the presence of sodium hydroxide. The proportions of the two solutions of the silicic and aluminum precursors are adjusted in such a way as to attain a composition of 70% $Al_2O_3$-30% $SiO_2$ in the final substrate. The reaction is carried out at a temperature of 60° C. with the pH value kept constant at around 7. The suspension thus obtained is then filtered, and the precipitate is washed successively with water and a solution of ammonium nitrate and then dried at 120° C. The powder thus prepared is shaped by a mixing in a Z-arm mixing machine. The extrusion is carried out by passing paste through a trilobed die of 2.5 mm. The extrudates thus obtained are dried at 150° C. and then calcined at 550° C. for 2 hours.

The characteristics of the substrate SA' are as follows:

The composition of the silica-alumina substrate is 70% $Al_2O_3$ and 30% $SiO_2$.

The BET surface area is 277 m²/g.

The total pore volume, measured by nitrogen adsorption, is 0.77 ml/g.

The mean pore diameter, measured by mercury porosimetry, is 9.5 Å.

The ratio between the volume V2, measured by mercury porosimetry, encompassed between $D_{mean}-30$ Å and $D_{mean}+30$ Å to the total mercury volume is 0.85.

The volume V3, measured by mercury porosimetry, encompassed in the pores of upper diameters with $D_{mean}+30$ Å is 0.045 ml/g.

The ratio between the volume V5, measured by mercury porosimetry, encompassed between $D_{mean}-15$ Å and $D_{mean}+15$ Å to the volume V2 above is 0.88.

The volume V6, measured by mercury porosimetry, encompassed in the pores with diameters of greater than $D_{mean}+15$ Å is 0.067 ml/g.

The ratio between the adsorption surface area and the BET surface area is 0.98.

The pore volume, measured by mercury porosimetry, encompassed in the pores with diameters of greater than 140 Å is 0.036 ml/g.

The pore volume, measured by mercury porosimetry, encompassed in the pores with diameters of greater than 160 Å is 0.033 ml/g.

The pore volume, measured by mercury porosimetry, encompassed in the pores with diameters of greater than 200 Å is 0.025 ml/g.

The pore volume, measured by mercury porosimetry, is [sic] encompassed in the pores with diameters of greater than 500 Å is 0.017 ml/g.

The atomic sodium content is 1200+/−20 ppm. The atomic sulfur content is not detected.

The value of the catalytic activity in the test for isomerization of m-xylene is 0.5 mmol·h⁻¹·$g_{solid}^{-1}$.

Implementation of the Catalytic Test

All of the catalysts described in the examples above are tested for approximately 100 hours in an identical way so as to compare their performances in terms of service life and development of the activity and selectivity. During this period, two conditions of temperature (300 and 400° C.) and of vvh [hourly volumetric flow rate] (0.7 and 5 h⁻¹) are studied. A point of return to the initial condition is created at the end of the test so as to verify the stability of the catalyst. 15 g of catalyst in the form of extrudates is used without any dilution of the catalytic bed by an inert solid.

Before the test itself, the activation of the solid at 550° C. is initiated in air for 2 hours. This activation consists in a calcination whose purpose is the combustion of traces of oil, fat and the drying of the catalyst before its use. The temperature is then lowered to the desired value to carry out the test. The injection of the alcohol feedstock is initiated when the test temperature is reached.

Example 3

Dehydration/Isomerization Activity of Isobutanol on the Catalysts According to Examples 1 to 2

A flow of commercial isobutanol containing 0.5% by weight of water is injected so as to reach the targeted hourly volumetric flow rate (0.7 or 5 h$^{-1}$). At the outlet of the reactor, all of the effluent is analyzed by an online injection by gas phase chromatography. With the online analyzing device being equipped with an FID detector, it does not make possible the quantification of hydrogen, CO or $CO_2$ that is optionally formed. However, the possible dehydrogenation reactions are followed using the analysis of isobutyraldehyde. The chromatographic method that is used makes possible the separation of isomers from butene and the identification of the oxidized molecules that are formed. The reaction conditions involved are: a temperature of 300 or 400° C., with the reactor being isothermal, and a pressure of 0.1 bar relative and an hourly volumetric flow rate of 0.7 or 5 h$^{-1}$.

The hydrocarbon portion of the effluent for the most part contains all of the isomers of the butenes and traces of propylene and pentenes, as well as traces of $C_1$, $C_2$, $C_3$, $C_5$ and $C_6$ hydrocarbons. The oxidized products that are formed (minority products) are: the dehydrogenation product (isobutyraldehyde) and diisobutyl ether (traces). The unconverted isobutanol is also analyzed. The results are presented in Tables 1 and 2. Only the majority compounds are reported as well as several minority radicals that are representative of the secondary reactions taking place (cracking, hydrogen transfer).

TABLE 1

(According to Example AS1)

| Catalyst AS1 | | Effluent | | | | |
|---|---|---|---|---|---|---|
| Time under Load | Feedstock | 5 Hours | 20 Hours | 40 Hours | 70 Hours | Return Point 100 Hours |
| Temperature (° C.) | | 300 | 300 | 400 | 400 | 300 |
| vvh (h$^{-1}$) | | 0.7 | 5 | 0.7 | 5 | 0.7 |
| % Radical | | | | | | |
| Propane | | 0.015 | 0 | 0.5 | 0.4 | 0.01 |
| Propylene | | 0 | 0 | 0 | 0 | 0 |
| Isobutane | | 0.429 | 0.3 | 0.8 | 0.3 | 0.35 |
| Butene-2-trans | | 11.2 | 10.2 | 15.5 | 14.3 | 11.1 |
| Butene-1 | | 5.8 | 4.2 | 7.6 | 7 | 5.8 |
| Isobutene | | 71 | 75.4 | 60.9 | 66 | 71.1 |
| Butene-2-cis | | 9.5 | 7.9 | 11.9 | 9.6 | 9.4 |
| C5+ Sum | | 1.75 | 1.4 | 2.75 | 2 | 1.65 |
| Isobutyraldehyde | | 0.23 | 0.1 | 0.01 | 0 | 0.22 |
| Butanone | | 0.06 | 0.02 | 0 | 0.01 | 0 |
| Isobutanol | 100 | 0.1 | 0.5 | 0 | 0.02 | 0.1 |
| Sum | | 100 | 100 | 100 | 100 | 100 |
| Conversion | | 99.9 | 99.5 | 100 | 99.8 | 99.9 |
| Selectivity of Linear Butenes in the C4 Olefins Fraction (%) | | 27.18 | 22.82 | 36.50 | 31.89 | 27.00 |
| C5+ Selectivity (%) | | 1.75 | 1.41 | 2.75 | 2.00 | 1.65 |
| Butenes Selectivity (%) | | 97.5 | 97.7 | 95.9 | 96.9 | 97.4 |

TABLE 2

(Comparison AS2)

| Catalyst AS2 | | Effluent | | | | |
|---|---|---|---|---|---|---|
| Time under Load | Feedstock | 5 Hours | 15 Hours | 35 Hours | 70 Hours | Return Point 100 Hours |
| Temperature (° C.) | | 300 | 300 | 400 | 400 | 300 |
| vvh (h$^{-1}$) | | 0.7 | 5 | 0.7 | 5 | 0.7 |
| % Radical | | | | | | |
| Propane | | 0.15 | 0.1 | 0.2 | 0.17 | 0.15 |
| Propylene | | 0.01 | 0 | 0.01 | 0.02 | 0.01 |
| Isobutane | | 0.3 | 0.1 | 0.4 | 0.36 | 0.35 |
| Butene-2-trans | | 12.1 | 11.9 | 13.5 | 12.2 | 10.2 |
| Butene-1 | | 3.2 | 2.9 | 3.1 | 3 | 2.2 |
| Isobutene | | 60 | 64.5 | 51.5 | 54.5 | 65 |
| Butene-2-cis | | 8.6 | 7.5 | 9.1 | 8.9 | 7.1 |
| C5+ Sum | | 15.4 | 12.8 | 22 | 20.8 | 14.2 |

TABLE 2-continued (Comparison AS2)

| Catalyst AS2 | | Effluent | | | | |
|---|---|---|---|---|---|---|
| Time under Load | Feedstock | 5 Hours | 15 Hours | 35 Hours | 70 Hours | Return Point 100 Hours |
| Isobutyraldehyde | | 0.1 | 0.05 | 0.12 | 0.15 | 0.1 |
| Butanone | | 0.01 | 0.01 | 0.01 | 0.02 | 0.01 |
| Isobutanol | 100 | 0.1 | 0.1 | 0 | 0 | 0.7 |
| Sum | | 100 | 100 | 100 | 100 | 100 |
| Conversion | | 99.9 | 99.5 | 100 | 100 | 99.3 |
| Selectivity of Linear Butenes in the C4 Olefins Fraction (%) | | 28.49 | 25.69 | 33.29 | 30.66 | 23.08 |
| C5+ Selectivity (%) | | 15.42 | 12.86 | 22.00 | 20.80 | 14.30 |
| Butenes Selectivity (%) | | 83.9 | 86.8 | 77.2 | 78.6 | 84.5 |

The catalyst according to the invention has an improved linear butene selectivity at 400° C. and very slightly less than 300° C. relative to AS2. It has a greater stability, and the linear butene selectivity is retained after 100 hours of testing whereas the solid AS2 has a significant loss of selectivity. In addition, the catalyst AS1 makes it possible to greatly limit the secondary reactions bringing about the formation of oligomers ($C_5^+$).

The invention claimed is:

1. A process for simultaneous dehydration and skeletal isomerization of a feedstock comprising at least one $C_4$ monoalcohol and between 0.5% by weight and 50% by weight of water to produce $C_4$ alkenes, the process comprising contacting the feedstock with a catalyst at a temperature of between 250° C. and 550° C., under a pressure of between 0.1 MPa and 1 MPa, and with an hourly volumetric flow rate of between 0.1 $h^{-1}$ and 10 $h^{-1}$, wherein the catalyst comprises at least one non-zeolitic aluminosilicate solid with a silica content of between 4% by weight and 95% by weight of said non-zeolitic aluminosilicate solid, said non-zeolitic aluminosilicate solid having the following further characteristics:

a total pore volume, measured by mercury intrusion porosimetry, of between 0.1 ml/g and 0.7 ml/g, a total pore volume, measured by nitrogen adsorption isotherm, of between 0.1 ml/g and 0.7 ml/g, a BET specific surface area of between 100 $m^2/g$ and 550 $m^2/g$, a pore volume, measured by mercury intrusion porosimetry, in pores with a diameter of greater than 140 Å, of less than 0.1 ml/g, a pore volume, measured by mercury intrusion porosimetry, in pores with a diameter of greater than 500 Å, of less than 0.01 ml/g, and a mean pore diameter of between 20 Å and 140 Å, and wherein said non-zeolitic aluminosilicate solid is prepared according to a process comprising the following stages:

stage a) forming a reaction mixture by mixing at least one aluminum compound that is partially soluble in an acid medium with either (i) at least one silicic compound that is totally soluble in the reaction mixture or (ii) a combination comprising the at least one silicic compound and the at least one aluminum compound, and obtaining a precursor solid, stage b) shaping said precursor solid, and stage c) subjecting said precursor solid to heat treatment and/or hydrothermal treatment with said stage c) being carried out before or after said stage b).

2. The process according to claim 1, wherein said feedstock has a mass ratio of isobutanol to all of the $C_4$ monoalcohols in the feedstock of greater than 50%.

3. The process according to claim 1, wherein said at least one silicic compound used in said stage a) is selected from the group consisting of a silicic acid, a silicic acid sol, a water-soluble alkaline silicate, and a cationic salt of silicon, and mixtures thereof.

4. The process according to claim 1, wherein said at least one aluminum compound used in said stage a) is selected from the group consisting of a boehmite, a pseudo-boehmite, and an amorphous or essential amorphous gel, and mixtures thereof.

5. The process according to claim 1, wherein said non-zeolitic aluminosilicate solid has a silica content of between 4% by weight and 25% by weight of said non-zeolitic aluminosilicate solid.

6. The process according to claim 1, wherein said non-zeolitic aluminosilicate solid has a silica content of between 4% by weight and 15% by weight of said non-zeolitic aluminosilicate solid.

7. The process according to claim 1, wherein said non-zeolitic aluminosilicate solid has a silica content of between 35% by weight and 95% by weight of said non-zeolitic aluminosilicate solid.

8. The process according to claim 1, wherein said non-zeolitic aluminosilicate solid has a silica content of between 35% by weight and 50% by weight of said non-zeolitic aluminosilicate solid.

9. The process according to claim 1, wherein said non-zeolitic aluminosilicate solid has a cationic impurities content of less than 0.1% by weight of the catalyst.

10. The process according to claim 1, wherein said non-zeolitic aluminosilicate solid has an anionic impurities content of less than 1% by weight of the catalyst.

11. The process according to claim 1, wherein said non-zeolitic aluminosilicate solid is homogenous on the micrometer scale.

12. The process according to claim 1, wherein acid properties of said non-zeolitic type aluminosilicate solid are such that its catalytic activity in the m-xylene isomerization test is between 0.02 $mmol \cdot h^{-1} g_{solid}^{-1}$ and 0.4 $mmol \cdot h^{-1} g_{solid}^{-1}$.

13. The process according to claim 1, wherein said catalyst integrally consists of the non-zeolitic aluminosilicate solid.

14. The process according to claim 1, wherein said non-zeolitic aluminosilicate solid is shaped in the form of spheres, spheroids, pellets or extrudates.

15. The process of claim 1, wherein the $C_4$ alkenes produced comprise isobutene and 1-butene.

16. The process of claim 1, wherein the feedstock is contacted with the catalyst at a temperature between 300° C. and 450° C., under a pressure of between 0.1 MPa and 0.5 MPa, and with an hourly volumetric flow rate of between 0.7 $h^{-1}$ and 5 $h^{-1}$.

17. The process according to claim 1, wherein the said non-zeolitic aluminosilicate solid has the following characteristics:

- a total pore volume, measured by mercury intrusion porosimetry, of between 0.1 ml/g and 0.5 ml/g,
- a total pore volume, measured by nitrogen adsorption isotherm, of between 0.1 ml/g and 0.5 ml/g,
- a BET specific surface area of between 150 $m^2/g$ and 350 $m^2/g$,
- a pore volume, measured by mercury intrusion porosimetry, in pores with a diameter of greater than 140 Å, of less than 0.05 ml/g,
- a pore volume, measured by mercury intrusion porosimetry, in pores with a diameter of greater than 500 Å, of less than 0.01 ml/g, and
- a mean pore diameter of between 20 Å and 140 Å.

* * * * *